(12) United States Patent
Kageyama

(10) Patent No.: US 11,554,408 B2
(45) Date of Patent: Jan. 17, 2023

(54) HOLLOW STRANDED WIRE

(71) Applicant: TOKUSEN KOGYO CO., LTD., Ono (JP)

(72) Inventor: Yoshinobu Kageyama, Ono (JP)

(73) Assignee: TOKUSEN KOGYO CO., LTD., Ono (JP)

(*) Notice: Subject to any disclaimer, the term of this patent is extended or adjusted under 35 U.S.C. 154(b) by 429 days.

(21) Appl. No.: 16/765,390

(22) PCT Filed: Sep. 11, 2018

(86) PCT No.: PCT/JP2018/033693
§ 371 (c)(1),
(2) Date: May 19, 2020

(87) PCT Pub. No.: WO2019/123735
PCT Pub. Date: Jun. 27, 2019

(65) Prior Publication Data
US 2020/0338625 A1 Oct. 29, 2020

(30) Foreign Application Priority Data

Dec. 20, 2017 (JP) .............................. JP2017-243472

(51) Int. Cl.
| | | |
|---|---|---|
| *B21F 3/00* | (2006.01) | |
| *D07B 1/06* | (2006.01) | |
| *A61M 25/00* | (2006.01) | |
| *A61M 25/09* | (2006.01) | |

(52) U.S. Cl.
CPC .............. *B21F 3/00* (2013.01); *D07B 1/0693* (2013.01); *A61M 25/005* (2013.01); *A61M 2025/09191* (2013.01)

(58) Field of Classification Search
None
See application file for complete search history.

(56) References Cited

U.S. PATENT DOCUMENTS

2007/0083132 A1  4/2007  Sharrow

FOREIGN PATENT DOCUMENTS

| JP | 03-068375 A | 3/1991 |
|---|---|---|
| JP | 08-071157 A | 3/1996 |
| JP | 2006-230635 A | 9/2006 |
| JP | 2009-511184 A | 3/2009 |

OTHER PUBLICATIONS

International Search Report for PCT/JP2018/033693 dated Nov. 20, 2018.

*Primary Examiner* — Daniel L Cerioni
*Assistant Examiner* — Benjamin S Melhus
(74) *Attorney, Agent, or Firm* — Sughrue Mion, PLLC

(57) ABSTRACT

A hollow stranded wire (2) has a first layers (4) and second layers (6). The second layer is located outside the first layer. The first layer is formed by twisting eight first element wires (8) which are flat wires. The second layer is formed by twisting eight second element wires (10) which are flat wires. A ratio (Ww/Tw) of a width Ww to a thickness Tw of each flat wire is from 2 to 11. A twisting direction of the second element wires is opposite that of the first element wires. A twisting angle of each first element wire is not greater than 85°. A twisting angle of each second element wire is not greater than 85°. A ratio (D/T) of an average diameter D to a thickness T of the hollow stranded wire is not less than 5 and not greater than 20.

6 Claims, 8 Drawing Sheets

HOLLOW STRANDED WIRE

CROSS REFERENCE TO RELATED APPLICATIONS

This application is a National Stage of International Application No. PCT/JP2018/033693 filed Sep. 11, 2018, claiming priority based on Japanese Patent Application No. 2017-243472 filed Dec. 20, 2017.

TECHNICAL FIELD

The present invention relates to hollow stranded wires suitable for medical devices, etc.

BACKGROUND ART

Medical devices that are inserted into body cavities are used for medical treatments such as endoscopy. JP2006-230635 discloses a medical device having a hollow coil. Another member is inserted into the hollow coil, and a medical treatment is performed.

As a hollow coil for a medical device, a coil formed by winding one wire has been known. A coil formed by winding two wires has also been known. A coil with a two-layer structure has also been known.

CITATION LIST

Patent Literature

Patent Literature 1: JP2006-230635

SUMMARY OF THE INVENTION

Problems to be Solved by the Invention

Since another member is inserted into a hollow coil, the coil preferably has a large inner diameter. Regarding a hollow coil obtained by winding one wire, when the inner diameter of the coil is set so as to be large, the coil easily stretches. This stretching impairs the pushability of the coil. Furthermore, when the coil is rotated in a direction opposite to the winding direction of the coil, looseness of twist easily occurs. The looseness of twist impairs the rotation followability of the coil.

The pushability of a hollow coil obtained by winding two wires is better than that of a hollow coil obtained by winding one wire. However, even the hollow coil obtained by winding two wires does not have sufficient rotation followability.

A hollow coil with a two-layer structure in which the winding direction of a first layer and the winding direction of a second layer are opposite to each other has excellent rotation followability. However, even this coil does not have sufficient pushability.

The present invention provides a hollow stranded wire having excellent pushability and rotation followability.

Solution to the Problems

A hollow stranded wire according to the present invention includes a first layer formed by twisting three or more first element wires, and a second layer formed by twisting three or more second element wires and located outside the first layer. The first element wires and/or the second element wires are each a flat wire. A twisting direction of the second element wires is opposite to a twisting direction of the first element wires. A ratio (D/T) of an average diameter D of the hollow stranded wire to a thickness T of the hollow stranded wire is not less than 5 and not greater than 20. A ratio (Ww/Tw) of a width Ww of the flat wire to a thickness Tw of the flat wire is not less than 2 and not greater than 11.

Preferably, each of the first element wires and the second element wires is a flat wire.

Preferably, a twisting angle of each first element wire is not greater than 85°. Preferably, a twisting angle of each second element wire is not greater than 85°.

Preferably, the flat wire is a rectangular wire.

According to another aspect, a medical device according to the present invention includes a hollow stranded wire. The hollow stranded wire includes a first layer formed by twisting three or more first element wires, and a second layer formed by twisting three or more second element wires and located outside the first layer. The first element wires and/or the second element wires are each a flat wire. A twisting direction of the second element wires is opposite to a twisting direction of the first element wires. A ratio (D/T) of an average diameter D of the hollow stranded wire to a thickness T of the hollow stranded wire is not less than 5 and not greater than 20. A ratio (Ww/Tw) of a width Ww of the flat wire to a thickness Tw of the flat wire is not less than 2 and not greater than 11.

According to still another aspect, a hollow stranded wire according to the present invention includes: a first layer formed by twisting three or more first element wires; a second layer formed by twisting three or more second element wires and located outside the first layer; and a third layer formed by twisting three or more third element wires and located outside the second layer. At least one of each first element wire, each second element wire, and each third element wire is a flat wire. A twisting direction of the second element wires is opposite to a twisting direction of the first element wires. A twisting direction of the third element wires is the same as the twisting direction of the first element wires. A ratio (D/T) of an average diameter D of the hollow stranded wire to a thickness T of the hollow stranded wire is not less than 5 and not greater than 20. A ratio (Ww/Tw) of a width Ww of the flat wire to a thickness Tw of the flat wire is not less than 2 and not greater than 11.

Advantageous Effects of the Invention

The hollow stranded wire according to the present invention has excellent pushability and rotation followability.

DESCRIPTION OF EMBODIMENTS

The following will describe in detail the present invention based on preferred embodiments with appropriate reference to the drawings.

Figure 1:
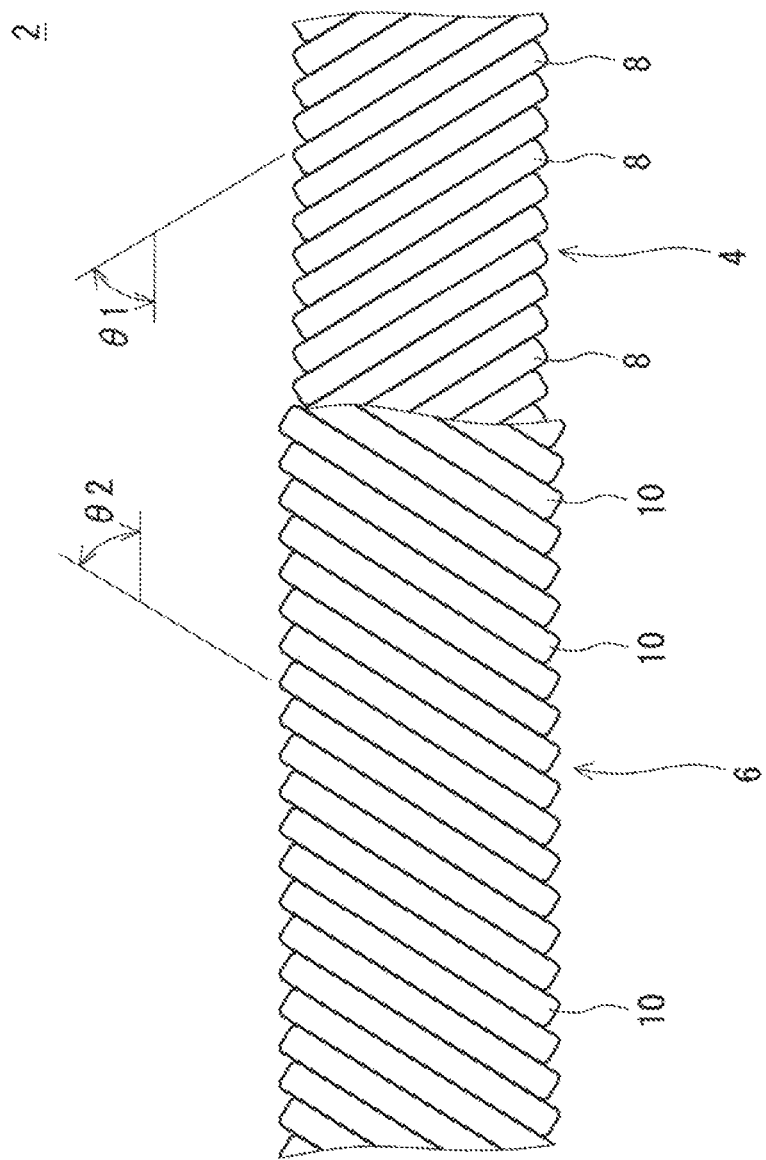
FIG. 1 is a front view showing a part of a hollow stranded wire according to an embodiment of the present invention.

FIG. 1 shows a hollow stranded wire 2. The hollow stranded wire 2 is formed from a metal material. The hollow stranded wire 2 is long. The hollow stranded wire 2 is cut into a predetermined length and used as a member of a medical device. For example, a base end portion of the hollow stranded wire 2 is connected to a hand operation part of the medical device, and a distal end portion of the hollow stranded wire 2 is connected to a treatment part of the medical device. Pushing force, pulling force, and torque applied to the base end portion are transmitted to the distal end portion via the hollow stranded wire 2. Accordingly, the treatment part makes a treatment motion. The medical device has the hollow stranded wire 2 and another member.

Figure 2:
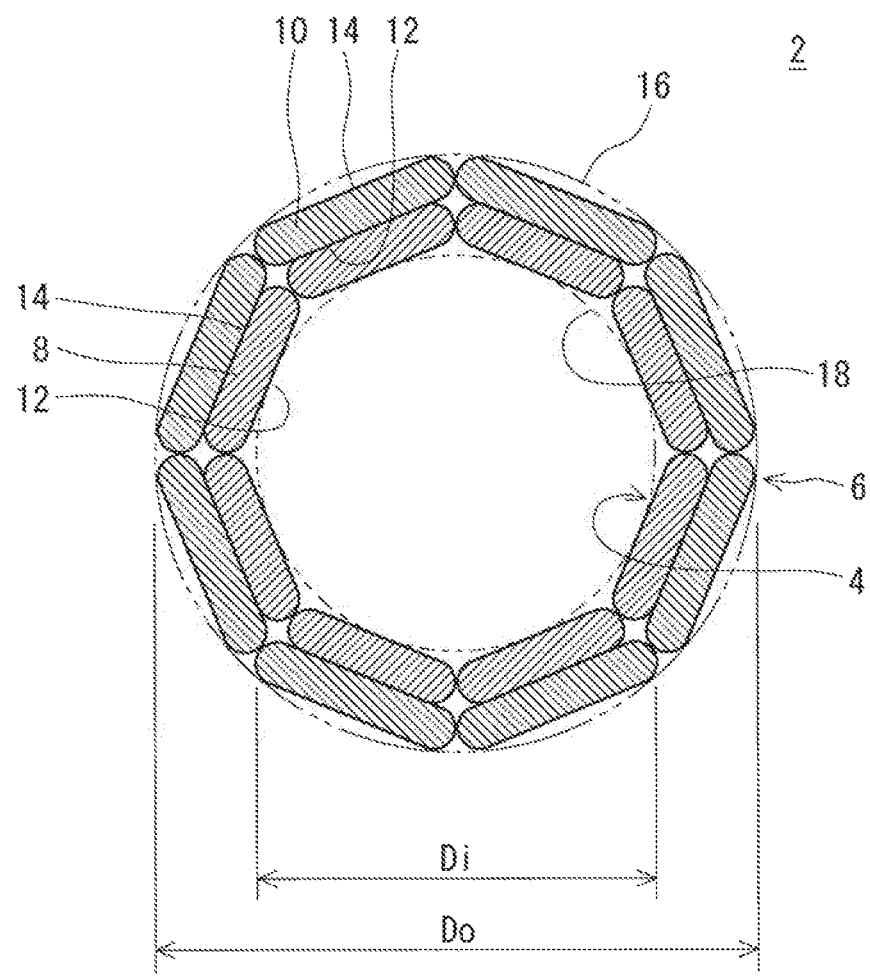
FIG. 2 is a schematic cross-sectional view showing the hollow stranded wire in FIG. 1.

FIG. 2 is an enlarged cross-sectional view of the hollow stranded wire 2. FIG. 2 shows a cross section of the hollow stranded wire 2 perpendicular to the longitudinal direction of the hollow stranded wire 2. As shown in FIGS. 1 and 2, the hollow stranded wire 2 has a first layer 4 and a second layer 6. The second layer 6 is located outside the first layer 4. The first layer 4 is formed by twisting eight first element wires 8. The second layer 6 is formed by twisting eight second element wires 10. Since FIG. 2 is a schematic cross-sectional view, cross-sections of the first element wires 8 are each depicted as a long circle, and cross-sections of the second element wires 10 are also each depicted as a long circle. In the actual hollow stranded wire 2, the cross-sections of the first element wires 8 each have an arc shape, and the cross-sections of the second element wires 10 also each have an arc shape. In FIG. 2, the cross-sections of the second element wires 10 are depicted with sizes larger than those of the cross-sections of the first element wires 8. In the actual hollow stranded wire 2, each second element wire 10 has a width (the meaning of the "width" will be described in detail later) equal to that of each first element wire 8. The widths of the second element wires 10 may be different from the widths of the first element wires 8.

As shown in FIG. 1, the twisting direction of the second element wires 10 is opposite to the twisting direction of the first element wires 8. In the present description, the twisting direction of the first element wires 8 is referred to as "Z direction", and the twisting direction of the second element wires 10 is referred to as "S direction". The first element wires 8 may be twisted in the "S direction", and the second element wires 10 may be twisted in the "Z direction".

Figure 3:
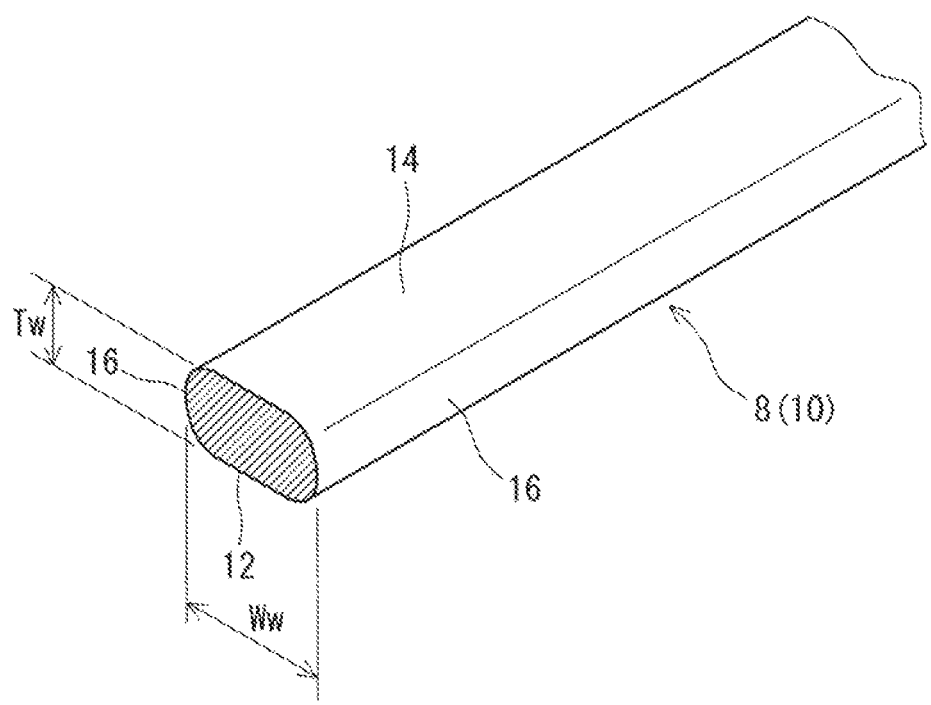
FIG. 3 is a perspective view showing a part of a first element wire of the hollow stranded wire in FIG. 1.

FIG. 3 is a perspective view showing a part of a first element wire 8. Each second element wire 10 also has the shape shown in FIG. 3. In other words, FIG. 3 is also a perspective view showing a second element wire 10. FIG. 3 shows the first element wire 8 (or the second element wire 10) in a state before being twisted. The first element wire 8 has an inner flat surface 12, an outer flat surface 14, and a pair of curved surfaces 16. In the present invention, an element wire that has an inner flat surface 12 and an outer flat surface 14 and in which the width thereof is larger than the thickness thereof is referred to as "flat wire". The first element wires 8 are flat wires. The second element wires 10 are also flat wires.

As is obvious from FIGS. 2 and 3, each first element wire 8 is twisted such that the inner flat surface 12 thereof faces the center. Each second element wire 10 is also twisted such that the inner flat surface 12 thereof faces the center.

An alternate long and two short dashes line shown by reference character 16 in FIG. 2 is the circumscribed circle of the hollow stranded wire 2. An arrow Do indicates the diameter of the circumscribed circle 16. In the present invention, the diameter Do is referred to as "outer diameter of the hollow stranded wire". From the viewpoint of easy insertion into a body cavity, the outer diameter Do is preferably not greater than 5.0 mm, more preferably not greater than 3.0 mm, and particularly preferably not greater than 2.0 mm.

An alternate long and two short dashes line shown by reference character 18 in FIG. 2 is the inscribed circle of the hollow stranded wire 2. An arrow Di indicates the diameter of the inscribed circle 18. In the present invention, the diameter Di is referred to as "inner diameter of the hollow stranded wire". From the viewpoint that the other member is easily passed through an interior, the inner diameter Di is preferably not less than 0.2 mm, more preferably not less than 0.5 mm, and particularly preferably not less than 1.0 mm.

In the present invention, an average diameter D of the hollow stranded wire 2 is calculated by the following mathematical formula.

$$D=(Do+Di)/2$$

In the present invention, a thickness T of the hollow stranded wire 2 is calculated by the following mathematical formula.

$$T=(Do-Di)/2$$

As described above, the first element wires 8 are flat wires, and the second element wires 10 are also flat wires. Therefore, the thickness T is relatively small. In other words, the ratio of the inner diameter Di to the outer diameter Do is relatively high. The hollow stranded wire 2 is easily inserted into a body cavity, and the other member is easily passed through the interior of the hollow stranded wire 2. From this viewpoint, the thickness T is preferably not greater than 0.50 mm, more preferably not greater than 0.40 mm, and particularly preferably not greater than 0.30 mm. In light of pushability and rotation followability, the thickness T is preferably not less than 0.05 mm, more preferably not less than 0.10 mm, and particularly preferably not less than 0.20 mm.

The ratio (D/T) of the average diameter D to the thickness T is preferably not less than 5 and not greater than 20. The other member is easily passed through the interior of the hollow stranded wire 2 in which the ratio (D/T) is not less than 5. From this viewpoint, the ratio (D/T) is more preferably not less than 6 and particularly preferably not less than 8. The hollow stranded wire 2 in which the ratio (D/T) is not greater than 20 has excellent pushability and rotation followability. From this viewpoint, the ratio (D/T) is more preferably not greater than 16 and particularly preferably not greater than 14.5.

In FIG. 3, an arrow Ww indicates the width of the first element wire 8 (or the second element wire 10), and an arrow Tw indicates the thickness of the first element wire 8 (or the second element wire 10). The width Ww is larger than the thickness T. The ratio (Ww/Tw) of the width Ww to the thickness Tw is preferably not less than 2 and not greater than 11. The hollow stranded wire 2 in which the ratio (Ww/Tw) is not less than 2 has excellent pushability. From this viewpoint, the ratio (Ww/Tw) is more preferably not less than 4 and particularly preferably not less than 6. The stiffness of the hollow stranded wire 2 in which the ratio (Ww/Tw) is not greater than 11 is not excessively high. Therefore, the hollow stranded wire 2 easily advances within a body cavity. Moreover, the element wires in which the ratio (Ww/Tw) is not greater than 11 are less likely to become deformed when being twisted. From these viewpoints, the ratio (Ww/Tw) is particularly preferably not greater than 10.

Flat wires do not need to be used for both the first layer 4 and the second layer 6. The first layer 4 may be formed from flat wires, and the second layer 6 may be formed from round wires. The first layer 4 may be formed from round wires, and the second layer 6 may be formed from flat wires. A round wire refers to an element wire having a circular contour shape in a cross-section perpendicular to the longitudinal direction thereof.

Ideally, both the first element wires 8 and the second element wires 10 are flat wires. In the hollow stranded wire 2, the second element wires 10 are in surface contact with the first element wires 8. The hollow stranded wire 2 has excellent pushability and rotation followability.

As described above, the first layer 4 is formed by twisting a plurality of the first element wires 8. Therefore, the first layer 4 is difficult to stretch. Furthermore, in the first layer 4, an inclination angle θ1 (see FIG. 1) of each first element wire 8 relative to the longitudinal direction is small. The first layer 4 can contribute to the pushability and rotation followability of the hollow stranded wire 2. From these viewpoints, the angle θ1 is preferably not greater than 85°, more preferably not greater than 80°, and particularly preferably not greater than 75°. The angle θ1 is preferably not less than 30°.

From the viewpoint that a small angle θ1 is achieved, the number of first element wires 8 in the first layer 4 is preferably not less than 3, more preferably not less than 6, and particularly preferably not less than 8. The number is preferably not greater than 12.

As described above, the second layer 6 is formed by twisting a plurality of the second element wires 10. Therefore, the second layer 6 is difficult to stretch. Furthermore, in the second layer 6, an inclination angle θ2 (see FIG. 1) of each second element wire 10 relative to the longitudinal direction is small. The second layer 6 can contribute to the pushability and rotation followability of the hollow stranded wire 2. From these viewpoints, the angle θ2 is preferably not greater than 85°, more preferably not greater than 80°, and particularly preferably not greater than 75°. The angle θ2 is preferably not less than 30°.

From the viewpoint that a small angle θ2 is achieved, the number of second element wires 10 in the second layer 6 is preferably not less than 3, more preferably not less than 6, and particularly preferably not less than 8. The number is preferably not greater than 12.

As described above, the twisting direction of the second element wires 10 is opposite to the twisting direction of the first element wires 8. When the hollow stranded wire 2 is rotated leftward, looseness of twist does not occur in the first layer 4. Therefore, the first layer 4 contributes to rotation followability. When the hollow stranded wire 2 is rotated rightward, looseness of twist does not occur in the second layer 6. Therefore, the second layer 6 contributes to rotation followability. The hollow stranded wire 2 has excellent rotation followability regardless of a rotation direction.

To produce the hollow stranded wire 2, first, a base wire is drawn and rolled to obtain the first element wires 8 and the second element wires 10. Next, a core wire is prepared. A plurality of the first element wires 8 are twisted around the core wire to form the first layer 4. A plurality of the second element wires 10 are twisted around the first layer 4 to form the second layer 6. The twisting direction of the second element wires 10 is opposite to the twisting direction of the first element wires 8. A stranded wire composed of the first layer 4 and the second layer 6 is subjected to a post heat treatment. The shapes of the first layer 4 and the second layer 6 are stabilized by the post heat treatment. After the heat treatment, the stranded wire is cut into a predetermined length. Furthermore, the core wire is pulled out from the first layer 4, whereby the hollow stranded wire 2 is obtained.

Figure 4:
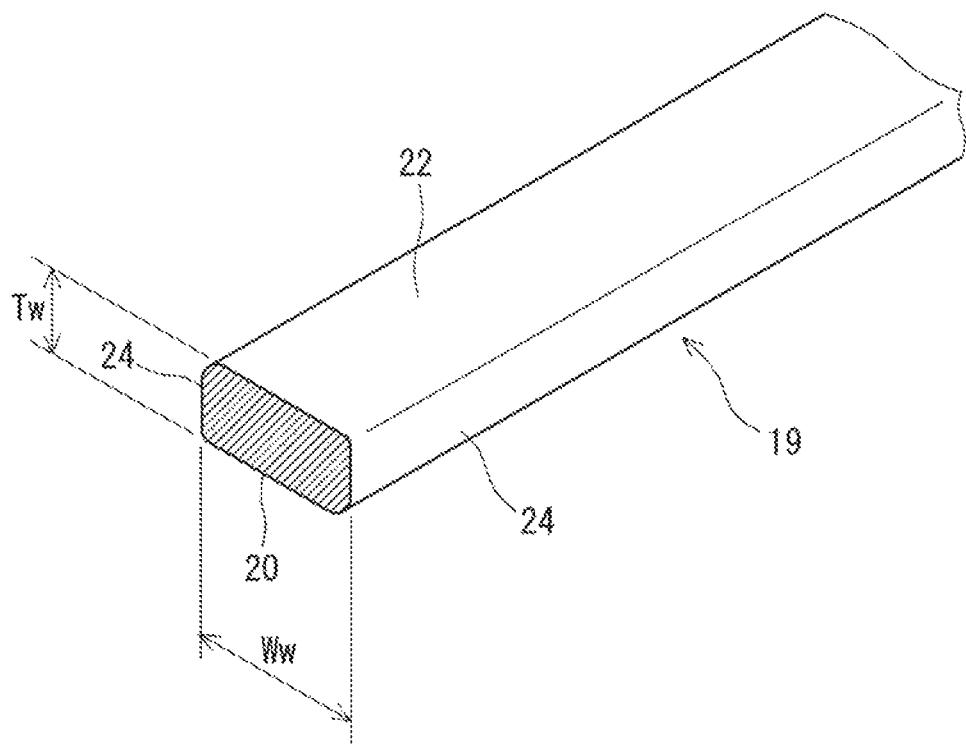
FIG. 4 is a perspective view showing an element wire of a hollow stranded wire according to another embodiment of the present invention.

FIG. 4 is a perspective view showing an element wire 19 of a hollow stranded wire according to another embodiment of the present invention. Similar to the hollow stranded wire 2 shown in FIG. 1, the hollow element wire has a first layer and a second layer. The first layer is formed by twisting three or more element wires 19. The second layer is formed by twisting three or more element wires 19.

The element wire 19 has an inner flat surface 20, an outer flat surface 22, and a pair of side flat surfaces 24. In the present invention, an element wire that has an inner flat surface 20, an outer flat surface 22, and a pair of side flat surfaces 24 and in which the width Ww thereof is larger than the thickness Tw thereof is referred to as "rectangular wire". The rectangular wire is also a flat wire. In a preferable rectangular wire, the thickness of each side flat portion 24 is not less than half the thickness Tw.

The side flat surfaces 24 of a rectangular wire 18 contact the side flat surfaces 24 of rectangular wires 18 adjacent thereto. This contact creates resistance force with respect to bending of the hollow stranded wire. A hollow stranded wire having the rectangular wires 18 has excellent pushability.

Figure 5:
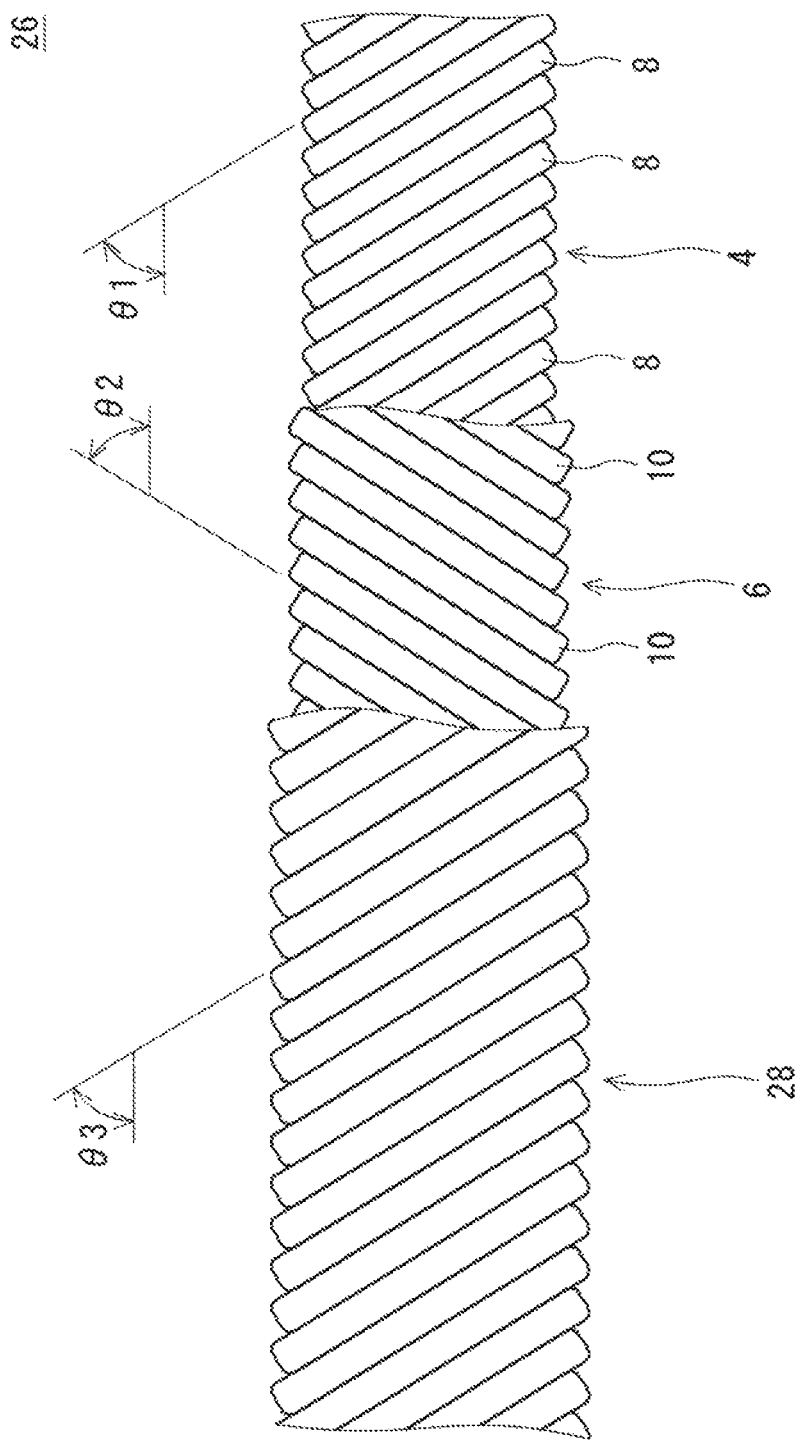
FIG. 5 is a front view showing a part of a hollow stranded wire according to still another embodiment of the present invention.

FIG. 5 is a front view showing a part of a hollow stranded wire 26 according to still another embodiment of the present invention. The hollow stranded wire 26 is also one member of a medical device. The hollow stranded wire 26 has a first layer 4, a second layer 6, and a third layer 28. Each of the first layer 4, the second layer 6, and the third layer 28 is formed by twisting three or more flat wires. In the present embodiment, the structures of the first layer 4 and the second layer 6 are the same as those of the hollow stranded wire 2 shown in FIGS. 1 to 3. In other words, the hollow stranded wire 26 has a structure in which the outer periphery of the hollow stranded wire 2 shown in FIGS. 1 to 3 is covered with the third layer 28. In the present embodiment, the third layer 28 is formed by twisting the flat wires 8 shown in FIG. 3. The number of flat wires 8 in the third layer 28 is eight.

As shown in FIG. 5, the twisting direction of the third layer 28 is the same as the twisting direction of the first layer 4 and is opposite to the twisting direction of the second layer. In the present embodiment, the twisting directions of the first layer 4 and the third layer 28 are the "Z direction", and the twisting direction of the second layer 6 is the "S direction". In the hollow stranded wire 26, looseness of twist can be inhibited. The twisting directions of the first layer 4 and the third layer 28 may be the "S direction", and the twisting direction of the second layer 6 may be the "Z direction".

In the hollow stranded wire 26 as well, the ratio (D/T) of the average diameter D to the thickness T is preferably not less than 5 and not greater than 20. Another member is easily passed through the interior of the hollow stranded wire 26 in which the ratio (D/T) is not less than 5. From this viewpoint, the ratio (D/T) is more preferably not less than 6 and particularly preferably not less than 8. The hollow stranded wire 26 in which the ratio (D/T) is not greater than 20 has excellent pushability and rotation followability. From this viewpoint, the ratio (D/T) is more preferably not greater than 16 and particularly preferably not greater than 14.5.

The flat wires 8 do not need to be used for all of the first layer 4, the second layer 6, and the third layer 28. The flat wires 8 may be used for any of these layers, and round wires may be used for the other layers. Ideally, the flat wires 8 are used for all of the first layer 4, the second layer 6, and the third layer 28. The rectangular wires 18 may be used for the first layer 4, the second layer 6, or the third layer 28.

In FIG. 5, reference character 83 indicates an inclination angle of each element wire of the third layer 28. In light of pushability and rotation followability of the hollow stranded wire 26, the angle θ3 is preferably not greater than 85°, more preferably not greater than 80°, and particularly preferably not greater than 75°. The angle θ3 is preferably not less than 30°.

From the viewpoint that a small angle θ3 is achieved, the number of element wires in the third layer 28 is preferably not less than 3, more preferably not less than 6, and particularly preferably not less than 8. The number is preferably not greater than 12.

EXAMPLES

The following will show the effects of the present invention by means of examples, but the present invention should not be construed in a limited manner based on the description of these examples.

Example 1

A steel material formed from SUS304 was subjected to wire drawing and rolling to obtain element wires (flat wires). The width Ww of each element wire was 0.27 mm, and the thickness Tw of each element wire was 0.045 mm. A first layer was formed by twisting eight flat wires on a core wire. The twisting direction of the first layer was the Z direction. A second layer was formed by twisting eight flat wires on the first layer. The twisting direction of the second layer was the S direction. A third layer was formed by twisting eight flat wires on the second layer. The twisting direction of the third layer was the Z direction. The inclination angle θ3 of each element wire of the third layer was 67°. A stranded wire composed of these element wires was subjected to a post heat treatment. The stranded wire was cut into a predetermined length. The core wire was pulled out from the stranded wire, to obtain a hollow stranded wire of Example 1. The outer diameter Do of the hollow stranded wire was 1.770 mm, and the inner diameter Di of the hollow stranded wire was 1.500 mm.

Examples 2 to 12, Conventional Examples 1 to 3, and Comparative Examples 1 to 3

Hollow stranded wires of Examples 2 to 12, Conventional Examples 1 to 3, and Comparative Examples 1 to 3 were obtained in the same manner as Example 1, except the configuration of each layer was as shown in Tables 1 to 4 below.

[Rotation Followability]

Figure 6:
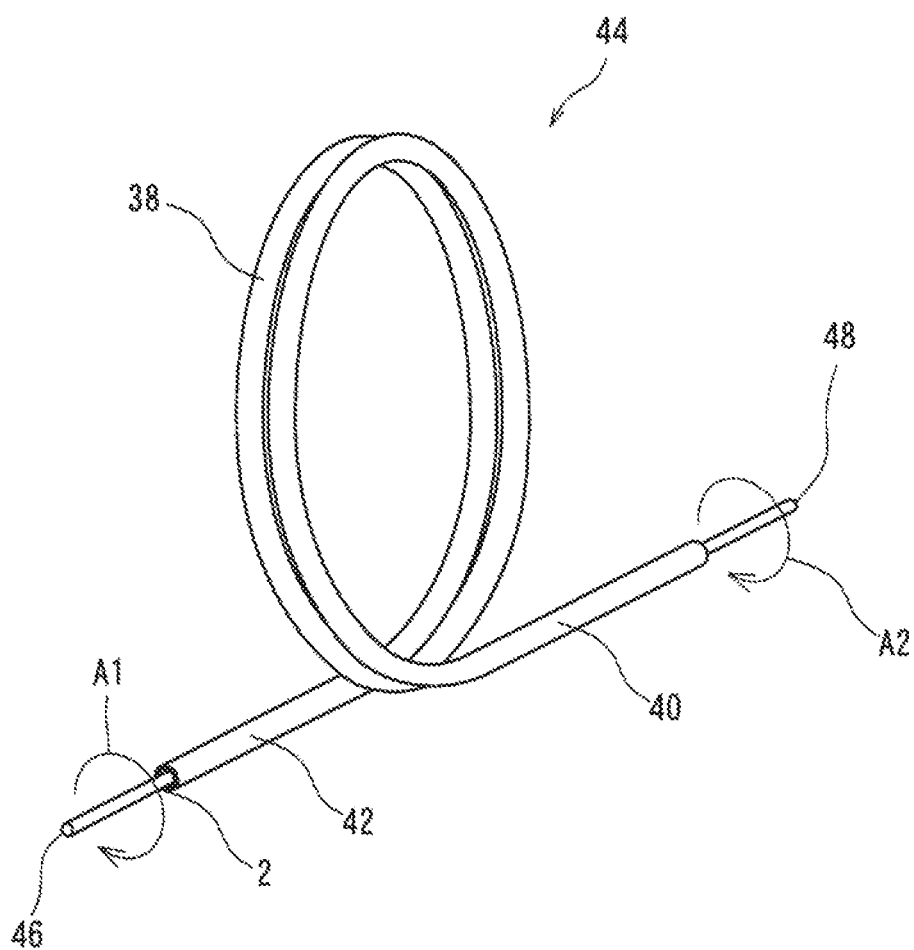
FIG. 6 is an explanatory diagram showing a method for measuring rotation followability of the hollow stranded wire in FIG. 1.

Rotation followability is evaluated on the basis of the difference between a rotation angle of the base end side and a rotation angle of the distal end side of a hollow stranded wire when the base end side was rotated. As shown in FIG. 6, a hard pipe 44 having a double spiral portion 38, a first straight portion 40, and a second straight portion 42 is prepared. The diameter of the double spiral portion 38 is 200 mm. A hollow stranded wire is passed through the hard pipe 44. Rotation force is applied to a base end side 46 of the hollow stranded wire in a direction indicated by an arrow A1 in FIG. 6. Accordingly, a distal end side 48 of the hollow stranded wire rotates as indicated by an arrow A2. The rotation angle of the base end side 46 and the rotation angle of the distal end side 48 are measured at the same time.

Figure 7:
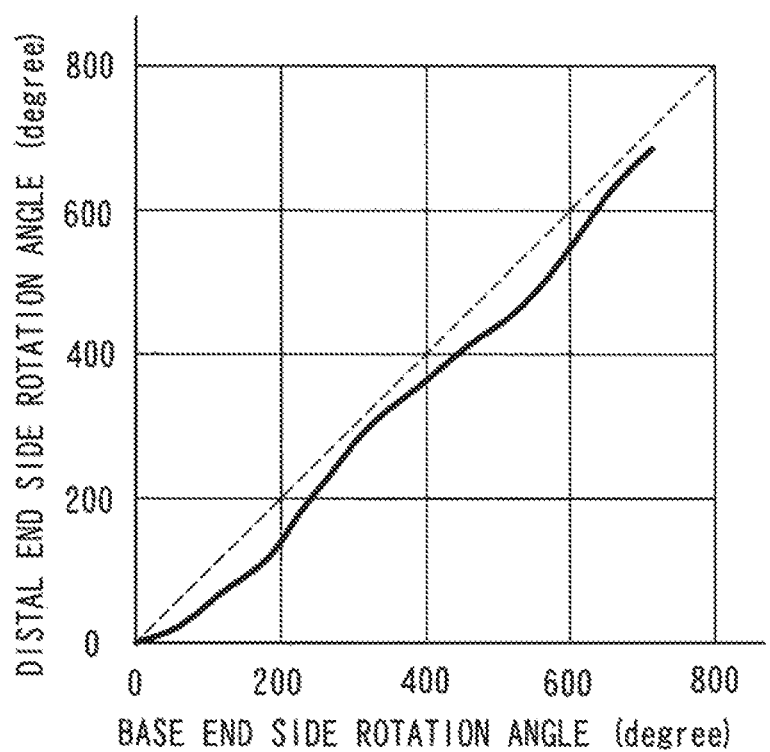
FIG. 7 is a graph showing the results of rotation followability measured by the method in FIG. 6.

FIG. 7 is a graph showing the results of rotation followability measured by the method in FIG. 6. In FIG. 7, the rotation angle of the base end side of a hollow stranded wire and the rotation angle of the distal end side at the same time are shown in association with each other. In other words, FIG. 7 is a graph showing a relationship between an input rotation angle and an output rotation angle of the hollow stranded wire. In the graph, a broken line is a straight line that indicates that the difference between the rotation angle of the base end side and the rotation angle of the distal end side is zero in the entire measurement angle range (an input rotation angle range from 0° to about 720°). The difference between the rotation angle of the base end side and the rotation angle of the distal end side of the hollow stranded wire to be measured is shown as the difference between the broken line in the figure and the measured value curve in the vertical axis direction. Among the rotation angle differences measured in the input rotation angle range from 0° to 720°, the maximum value is a value that correlates with rotation followability. The maximum value of the angle difference of each hollow stranded wire is shown as an index in Tables 1 to 4 below. A hollow stranded wire for which this index is low has excellent rotation followability.

[Stiffness]

Figure 8:
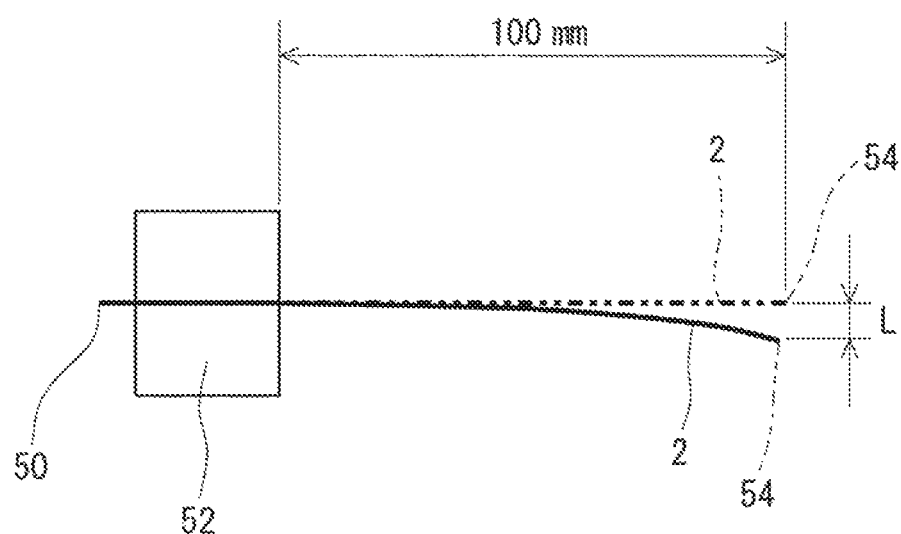
FIG. 8 is an explanatory diagram showing a method for measuring pushability of the hollow stranded wire in FIG. 1.

As shown in FIG. 8, a portion, of the hollow stranded wire 2, near a first end 50 was chucked with a jig 52. The distance from the jig 52 to a second end 54 of the hollow stranded wire 2 was 100 mm. The hollow stranded wire 2 was bent by its own weight, and the second end 54 moved downward. This movement distance L was measured. The movement distance L is shown as an index in Tables 1 to 4 below. The stiffness of a hollow stranded wire for which this index is low is high. A hollow stranded wire for which this index is low has excellent pushability.

TABLE 1

| | Evaluation Results | | | |
|---|---|---|---|---|
| | Example 1 | Example 2 | Example 3 | Example 4 |
| Number of element wires per layer | 8 | 8 | 8 | 8 |
| Number of layers | 3 | 3 | 3 | 3 |
| Element wire shape first/second/third | Flat/flat/flat | Round/flat/flat | Flat/flat/round | Flat/round/flat |
| Twisting direction first/second/third | Z/S/Z | Z/S/Z | Z/S/Z | Z/S/Z |
| Element wire dimensions (mm) first layer/ second layer/ third layer/ | 0.045*/0.27/0.045*/0.27/0.045*/0.27 | φ0.122/0.045*/0.27/0.27 | 0.045*/0.27/0.045*/0.27/φ0.122 | 0.045*/0.27/φ0.122/0.045*/0.27 |
| Do (mm) | 1.770 | 1.774 | 1.774 | 1.774 |
| Di (mm) | 1.500 | 1.350 | 1.350 | 1.350 |
| D/T | 12.1 | 7.4 | 7.4 | 7.4 |
| Ww/Tw of flat wire | 6.0 | 6.0 | 6.0 | 6.0 |
| Angle θ (°) of Outermost layer | 67 | 67 | 79 | 67 |

TABLE 1-continued

Evaluation Results

|  | Example 1 | Example 2 | Example 3 | Example 4 |
|---|---|---|---|---|
| Rotation angle difference (index) | 58 | 66 | 68 | 71 |
| Sag length L (index) | 100 | 98 | 100 | 98 |

TABLE 2

Evaluation Results

|  | Example 5 | Example 6 | Example 7 | Conventional Example 1 |
|---|---|---|---|---|
| Number of element wires per layer | 8 | 8 | 8 | 8 |
| Number of layers | 3 | 3 | 3 | 3 |
| Element wire shape first/second/third | Round/round/flat | Round/flat/round | Flat/round/round | Round/round/round |

TABLE 2-continued

Evaluation Results

|  | Example 5 | Example 6 | Example 7 | Conventional Example 1 |
|---|---|---|---|---|
| Twisting direction first/second/third | Z/S/Z | Z/S/Z | Z/S/Z | Z/S/Z |
| Element wire dimensions (mm) first layer/ second layer/ third layer | φ0.122/ φ0.122/ 0.045* 0.27 | φ0.122/ 0.045* 0.27/ φ0.122 | 0.045* 0.27/ φ0.122/ φ0.122 | φ0.122/ φ0.122/ φ0.122 |
| Do (mm) | 1.768 | 1.768 | 1.768 | 1.772 |
| Di (mm) | 1.190 | 1.190 | 1.190 | 1.040 |
| D/T | 5.1 | 5.1 | 5.1 | 4.1 |
| Ww/Tw of flat wire | 6.0 | 6.0 | 6.0 | — |
| Angle θ (°) of Outermost layer | 67 | 79 | 79 | 79 |
| Rotation angle difference (index) | 75 | 73 | 75 | 100 |
| Sag length L (index) | 100 | 98 | 100 | 100 |

TABLE 3

Evaluation Results

|  | Example 8 | Example 9 | Example 10 | Conventional Example 2 | Conventional Example 3 |
|---|---|---|---|---|---|
| Number of element wires per layer | 8 | 8 | 8 | 8 | 8 |
| Number of layers | 2 | 2 | 2 | 2 | 1 |
| Element wire shape first/second/third | Flat/flat | Round/flat | Flat/round | Round/round | Flat |
| Twisting direction first/second/third | Z/S | Z/S | Z/S | Z/S | Z |
| Element wire dimensions (mm) first layer/ second layer/ third layer/ | 0.055* 0.31/ — | φ0.145/ 0.055* — | 0.055* 0.31/ — | φ0.145/ φ0.145/ — | 0.100* 0.20/ — |
| Do (mm) | 1.380 | 1.380 | 1.380 | 1.380 | 1.100 |
| Di (mm) | 1.160 | 0.980 | 0.980 | 0.800 | 0.900 |
| D/T | 11.5 | 5.9 | 5.9 | 3.8 | 10.0 |
| Ww/Tw of flat wire | 5.6 | 5.6 | 5.6 | — | 2.0 |
| Angle θ (°) of Outermost layer | 53 | 73 | 53 | 73 | 59 |
| Rotation angle difference (index) | 86 | 91 | 89 | 104 | 114 |
| Sag length L (index) | 98 | 100 | 98 | 98 | 102 |

TABLE 4

Evaluation Results

|  | Comparative Example 1 | Comparative Example 2 | Comparative Example 3 | Example 11 | Example 12 |
|---|---|---|---|---|---|
| Number of element wires per layer | 8 | 12 | 8 | 8 | 12 |
| Number of layers | 3 | 3 | 3 | 3 | 3 |
| Element wire shape first/second/third | Flat/flat/flat | Flat/flat/flat | Flat/flat/flat | Square/square/square | Flat/flat/flat |

TABLE 4-continued

Evaluation Results

| | Comparative Example 1 | Comparative Example 2 | Comparative Example 3 | Example 11 | Example 12 |
|---|---|---|---|---|---|
| Twisting direction first/second/third | Z/Z/Z | Z/S/Z | Z/S/Z | Z/S/Z | Z/S/Z |
| Element wire dimensions (mm) first layer/ second layer/ third layer/ | 0.045*<br>0.27/<br>0.045*<br>0.27/<br>0.045*<br>0.27 | 0.025*<br>0.25/<br>0.025*<br>0.25/<br>0.025*<br>0.25 | 0.055*<br>0.10/<br>0.055*<br>0.10/<br>0.055*<br>0.10 | 0.045*<br>0.27/<br>0.045*<br>0.27/<br>0.045*<br>0.27 | 0.038*<br>0.38/<br>0.038*<br>0.38/<br>0.038*<br>0.38 |
| Do (mm) | 1.770 | 1.780 | 1.780 | 1.770 | 1.798 |
| Di (mm) | 1.500 | 1.630 | 1.450 | 1.500 | 1.570 |
| D/T of flat wire | 12.1 | 22.7 | 9.8 | 12.1 | 14.8 |
| Ww/Tw | 6.0 | 10.0 | 1.8 | 6.0 | 10.0 |
| Angle θ (°) of Outermost layer | 67 | 57 | 87 | 67 | 34 |
| Rotation angle difference (index) | 111 | 122 | 117 | 43 | 46 |
| Sag length L (index) | 98 | 132 | 134 | 94 | 98 |

As shown in Tables 1 to 4, the hollow stranded wire of each Example has excellent rotation followability and pushability. From the evaluation results, advantages of the present invention are clear.

INDUSTRIAL APPLICABILITY

The hollow stranded wire according to the present invention can be applied to various medical devices.

DESCRIPTION OF THE REFERENCE CHARACTERS 2, 26 . . . hollow stranded wire
4 . . . first layer
6 . . . second layer
8 . . . first element wire
10 . . . second element wire
19 . . . element wire
28 . . . third layer

The invention claimed is:

1. A hollow stranded wire comprising:
a first layer formed by twisting three or more first element wires; and
a second layer formed by twisting three or more second element wires and located outside the first layer, wherein
the first element wires and/or the second element wires are each a flat wire,
a twisting direction of the second element wires is opposite to a twisting direction of the first element wires,
a ratio (D/T) of an average diameter D of the hollow stranded wire to a thickness T of the hollow stranded wire is not less than 5 and not greater than 20, and
a ratio (Ww/Tw) of a width Ww of the flat wire to a thickness Tw of the flat wire is not less than 2 and not greater than 11.

2. The hollow stranded wire according to claim 1, wherein each of the first element wires and the second element wires is a flat wire.

3. The hollow stranded wire according to claim 1, wherein a twisting angle of each first element wire is not greater than 85°, and a twisting angle of each second element wire is not greater than 85°.

4. The hollow stranded wire according to claim 1, wherein the flat wire is a rectangular wire.

5. A medical device comprising a hollow stranded wire, wherein
the hollow stranded wire includes a first layer formed by twisting three or more first element wires, and a second layer formed by twisting three or more second element wires and located outside the first layer,
the first element wires and/or the second element wires are each a flat wire,
a twisting direction of the second element wires is opposite to a twisting direction of the first element wires,
a ratio (D/T) of an average diameter D of the hollow stranded wire to a thickness T of the hollow stranded wire is not less than 5 and not greater than 20, and
a ratio (Ww/Tw) of a width Ww of the flat wire to a thickness Tw of the flat wire is not less than 2 and not greater than 11.

6. A hollow stranded wire comprising:
a first layer formed by twisting three or more first element wires;
a second layer formed by twisting three or more second element wires and located outside the first layer; and
a third layer formed by twisting three or more third element wires and located outside the second layer, wherein
at least one of each first element wire, each second element wire, and each third element wire is a flat wire,
a twisting direction of the second element wires is opposite to a twisting direction of the first element wires,
a twisting direction of the third element wires is the same as the twisting direction of the first element wires,
a ratio (D/T) of an average diameter D of the hollow stranded wire to a thickness T of the hollow stranded wire is not less than 5 and not greater than 20, and
a ratio (Ww/Tw) of a width Ww of the flat wire to a thickness Tw of the flat wire is not less than 2 and not greater than 11.

* * * * *